United States Patent [19]

Leyva

[11] Patent Number: 5,772,654
[45] Date of Patent: Jun. 30, 1998

[54] APPARATUS FOR BREAST REDUCTION SURGERY

[76] Inventor: Horacio A. Leyva, 16000 Kingsmoore Way, Miami Lakes, Fla. 33014

[21] Appl. No.: 555,636

[22] Filed: Nov. 8, 1995

[51] Int. Cl.$^6$ .................................................. A61B 17/00
[52] U.S. Cl. .............................. 606/1; 128/897; 606/148; 606/232; 604/73
[58] Field of Search .............................. 606/1, 148, 232, 606/130; 604/73; 128/897, 898, 704

[56] References Cited

U.S. PATENT DOCUMENTS

| | | | |
|---|---|---|---|
| 4,608,977 | 9/1986 | Brown | 606/130 |
| 5,201,742 | 4/1993 | Hasson | 606/1 |
| 5,437,280 | 8/1995 | Hussman | 128/653.2 |
| 5,443,502 | 8/1995 | Caudillo et al. | 606/1 |
| 5,496,304 | 3/1996 | Chasan | 606/1 |

*Primary Examiner*—Lee S. Cohen
*Assistant Examiner*—Rosalind Kearney
*Attorney, Agent, or Firm*—Malloy & Malloy, P.A.

[57] ABSTRACT

An apparatus for use in breast reduction surgery including a shield body defining a substantially circular opening therein which is sized, dimensioned and configured to correspond the areola of a patient's breast, the shield body including a plurality of apertures for being removably fastened to the breast and a handle for lifting the shield body during surgery after having been attached to the breast, and a marker for penetrating into the breast tissue to form marking tracks which act as a cutting guide. The shield body includes a plurality of elongated tubular structures secured to an outer edge of the shield body at a predetermined angle relative to the shield body. Each elongated tubular structure having an elongated body with an opening at a first top end and at a second bottom end, the elongated body being hollow between the ends, and being structured and disposed to permit at least partial passage of the marker therethrough. The marker is structured and disposed to pass partially through the elongated tubular structures and to create marking tracks in the breast tissue to guide the surgeon with cutting and removing sections of breast tissue during the surgery such that following surgery, a patient's left and right breasts will be proportionate to each other, with the nipples of each properly positioned, and will have adequate circulation to and sensation within the nipple and areola portions of the breasts.

21 Claims, 4 Drawing Sheets

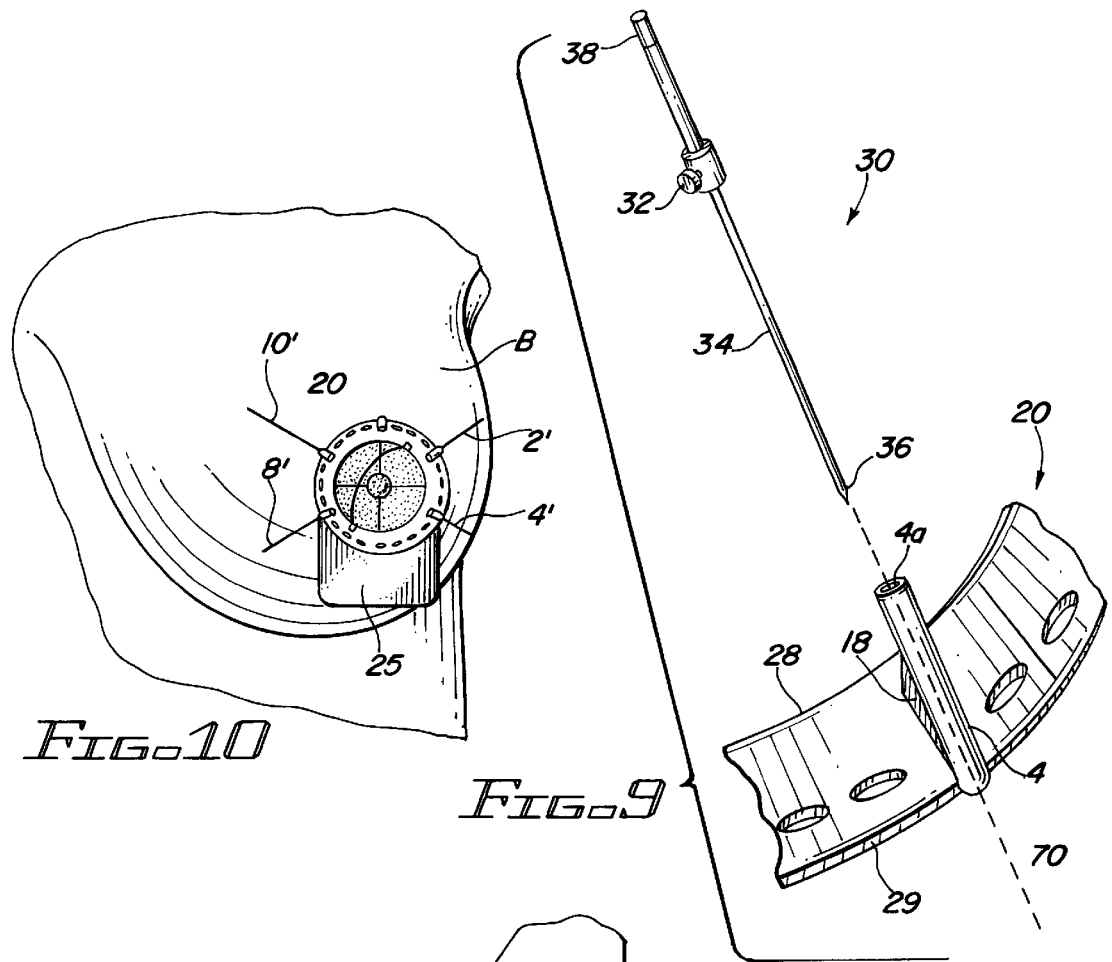
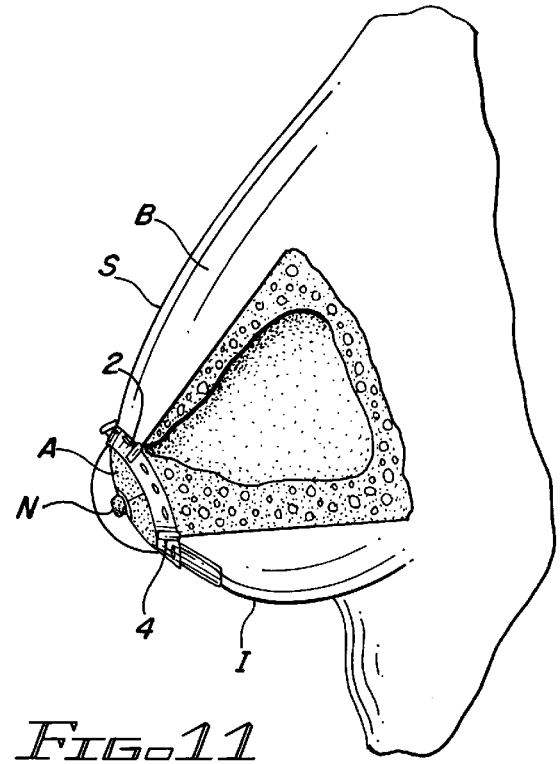

APPARATUS FOR BREAST REDUCTION SURGERY

BACKGROUND OF THE INVENTION

1. Field of the Invention

The present invention relates to an breast reduction apparatus for use during a breast reduction surgery and a method of employing the breast reduction apparatus.

2. Description of the Related Art

In current times, plastic surgery is quite commonly used to alter and improve a person's looks. In some cases, certain women having large bosoms view their bosom size as an impediment and wish to have their breast size reduced. Thus, breast reduction surgery, also referred to as reduction mammaplasty procedure, has become fairly common in recent years. Many medical practitioners regularly perform reduction mammaplasty procedures and a number of surgical procedures are considered standard to accomplish a breast reduction. For example, in Aesthetic Plastic Surgery, Rees, Saunders Company, 1980, Volume II, Chapter 33, incorporated herein by reference, a number of well known reduction mammaplasty procedures are described. Among the relevant procedures are the Aries-Pitanguy and McKissock techniques and in each, a lateral wedge technique is typically required which is difficult to master. Consequently, consistent good results, particularly with large breasts, are difficult to achieve. A problem exists in that current surgical techniques used during a breast reduction, including those referred to above, do not ensure that the patient's breasts will be proportionate nor that both nipples will be appropriately positioned on the breasts after the reduction mammaplasty is performed. Another potential undesirable result of breast reduction surgery is that the nipples on the patient's reduced breasts may have a "cross-eyed" appearance. It can be said that current techniques for breast reduction surgery regularly require some guesswork by the physician. For example, while a surgeon may slowly yet repeatedly remove breast tissue from the second of the two breasts and measure same until it equals that of the breast tissue removed from the first breast, this still does not ensure the breasts will be proportionate after surgery. Consequently, only those surgeons which are highly experienced in breast reductions surgery are capable of offering the finest results.

Another problem exists in that during most breast reduction surgeries, regardless of the technique used, several clamps are attached to the nipple portion of the breast and are used by an assistant to pull the nipple and surrounding breast tissue upwardly at right angles to the patient while the surgeon cuts away breast tissue. The number of clamps needed to effectively accomplish this generally requires that an assistant stand next to the patient (on the patient's side where the breast is that is being reduced) and use both hands in order to elevate the nipple portion secured within the clamp, including the breast tissue surrounding the nipple. Consequently, the surgeon who also works next to the patient (on the patient's side where the breast is that is being reduced) is forced to work around the assistant and his or her arms, all of which tends to complicate an already intricate surgical procedure.

SUMMARY OF THE INVENTION

The present invention seeks to overcome the problems associated with performing a breast reduction surgery on a patient by providing a breast reduction apparatus and method for using same. The apparatus comprises a shield having a body which is sized, dimensioned and configured for positioning on a portion of a patient's breast and defining a substantially circular opening therein, means for removably fastening the shield on the breast, and a plurality of elongated, tubular structures, each being operably connected to the shield at a predetermined angle about an outer periphery thereof. The apparatus will preferably include means on the shield for lifting the shield when fastened to the breast and preferably will also include a marker sized and configured for passage through the elongated tubular structures, and having an interior chamber in fluid communication with an open tip at one end thereof, a stopper, and a bovie, for use in penetrating and marking tissue within the patient's breast.

The present invention further includes a method for use during a breast reduction surgery which comprises the steps of positioning and removably fastening the shield on a patient's breast, lifting the shield and breast tissue fastened thereto to position the breast, passing the marker into each of the elongated tubular structures and into the breast tissue, opening a track in the breast tissue, marking each track, and removing portions of the breast in accordance with the markings made.

A primary objective of the present invention is to provide a device and method for use during surgery to reduce a patient's breast size that will result in the patient's breasts being proportionate to each other.

Another object of the present invention and method is to ensure that the nipple on each breast is appropriately positioned on each breast after the breast has been reduced in size.

An advantage of the present invention and method is that the nipples on the patient's breasts will be appropriately positioned relative to each other.

Yet another objective of the present invention and method is to preserve blood circulation to the breast after a breast reduction has taken place, and further, to preserve sensation and the nervous tissues in and around the breast nipple.

It is still another object of the present invention and method to minimize the extreme dangers associated with an inadvertent penetration into the patient's chest cavity during breast reduction surgery.

Other objects, features and advantages of this invention will become apparent from the drawings and the following description.

BRIEF DESCRIPTION OF THE DRAWINGS

For a fuller understanding of the nature of the present invention, reference should be had to the following detailed description taken in connection with the accompanying drawings in which:

FIG. 9 is a broken partial view of the shield body.

FIG. 10 is a front elevational view of a breast with incisions thereon.

FIG. 11 is a side elevational view of a breast after a medical practitioner has removed breast tissue.

Like reference numerals refer to like parts throughout the several views of the drawings.

DETAILED DESCRIPTION OF THE PREFERRED EMBODIMENT

Figure 4:
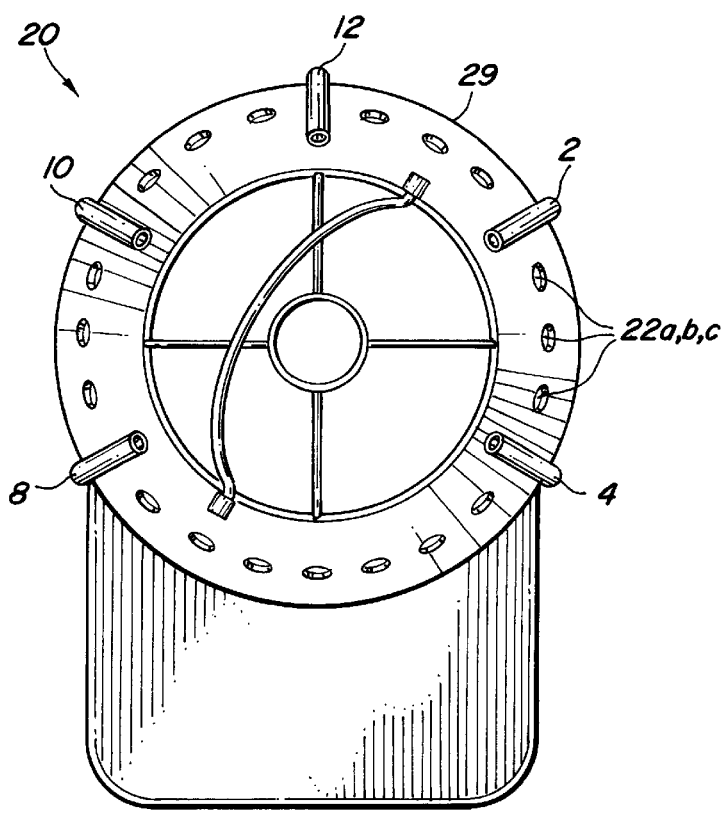
FIG. 4 is a top elevational view of the shield body shown in FIG. 3.
Figure 5:
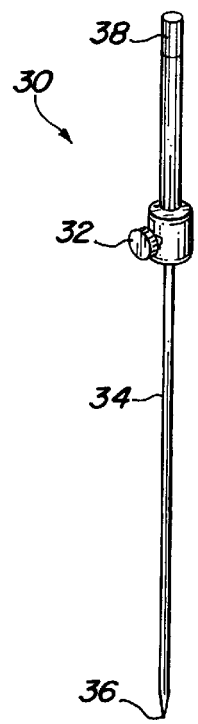
FIG. 5 is a side isometric view of the marker of the present invention.
Figure 6:
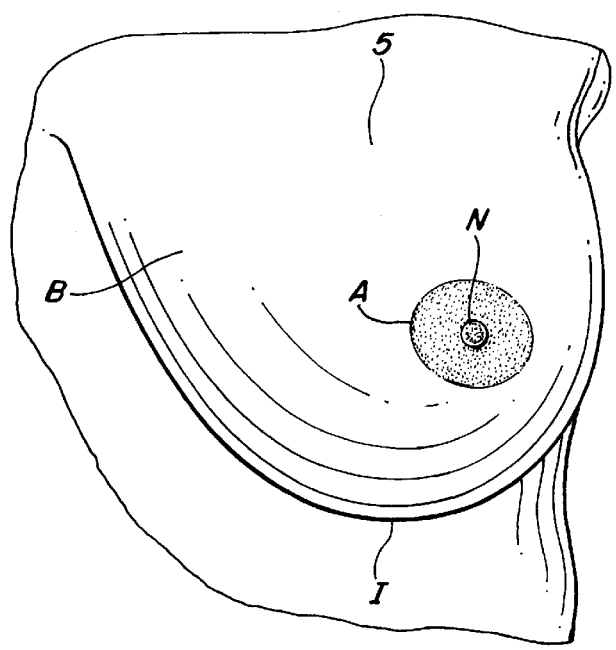
FIG. 6 is a front elevational view of a breast.

Referring now to FIGS. 1–11, the apparatus of the present invention for use during a breast reduction surgery is generally indicated at 20, and is seen to comprise a shield. A breast to be reduced is best shown in FIG. 6 and is seen to include a breast B, areola A, and nipple N.

Figure 3:
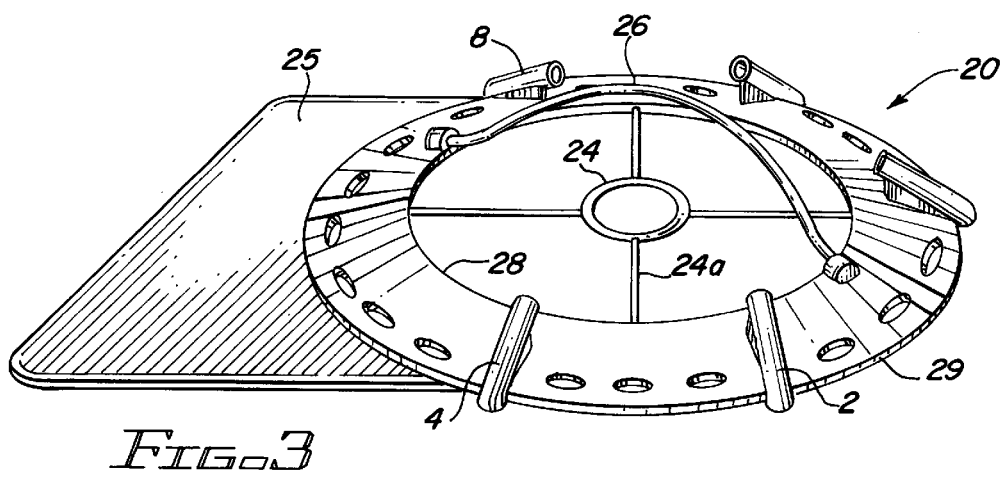
FIG. 3 is an isometric view of a preferred embodiment of the present invention.
Figure 7:
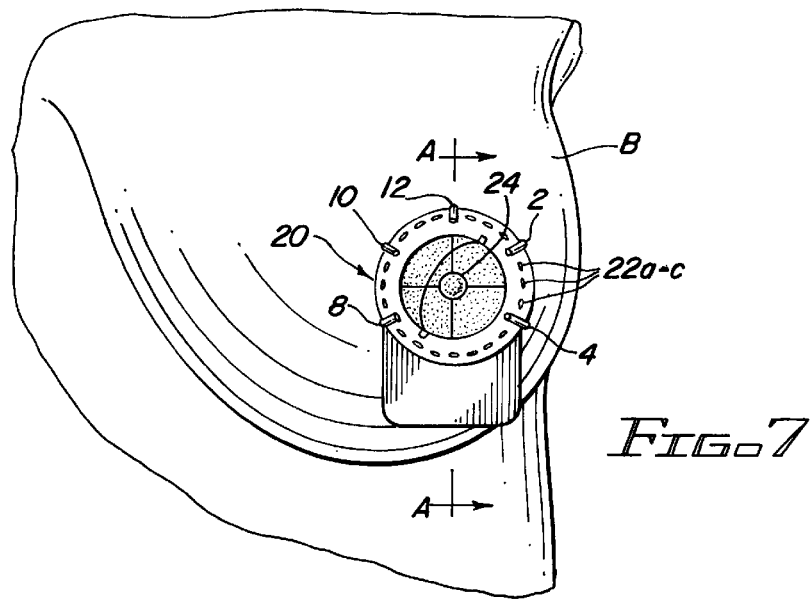
FIG. 7 is an elevational view of the preferred embodiment of the shield body secured in position on the breast of a reduction mammaplasty patient.

Shield 20 comprises a generally flat body which is sized, dimensioned and configured for positioning onto a portion of a patient's breast and defines a substantially circular opening. In particular, shield body 20 includes an inner edge 28 about and defining the substantially circular opening, and an outer edge 29. In the preferred embodiment, the substantially circular opening defined by the shield body will have a diameter of about 42 millimeters, whereas the overall shield body 20 is preferably sized to substantially correspond the outer circumference of the breast's areola A, as shown in FIGS. 6 and 7 and as such, may have a width from inner edge 28 to outer edge 29 of approximately 75 millimeters. Because the shield body is to be placed over and secured to the areola portion of a breast, which by its nature is not completely flat, the preferred embodiment of the shield body will also be formed to have a slightly domed-shape so as to conform to the breast's curvature. Also, it is contemplated that shield 20 will be made in a variety of sizes to readily accommodate patients of varying breast size, although preferably, shield body 20 will be made in three sizes, namely, small, medium and large, to accommodate most women. Ideally, shield body 20 will be integrally formed of a metallic material such as stainless steel or aluminum, although it could also be formed of a suitably strong plastic material as well. In one embodiment and as shown in the drawings, shield body 20 is substantially circular in shape. However, it will be appreciated by those skilled in the art that outer shield edge 29 could be configured in another shape such as an octagon, square, etc. although as shown in FIGS. 3 and 4, a most preferred embodiment of shield body 20 includes a lip member 25 extending therefrom, which will be described below.

As best seen in FIGS. 1–4, shield body 20 includes means for removably fastening the shield onto the breast. These fastening means may comprise a plurality of apertures formed within the shield body 20 for suturing the shield to the breast although clamps may accomplish this purpose as well. In the preferred embodiment, and as shown in the drawings, a plurality of suture holes 22a–22d are formed in shield body 20, along an exposed top surface thereof and are arranged substantially along an outer periphery thereof to permit a medical practitioner to removably fasten shield 20 to breast B, and preferably, with a continuous suture. In the preferred embodiment, the plurality of suture openings or holes are disposed in a generally circular arrangement on the shield body 20, as shown in the Figures. Of course, it will be appreciated that the apparatus of this invention would work suitably as well with less apertures and in a different arrangement on the shield body than are shown in the drawings.

Figure 2:
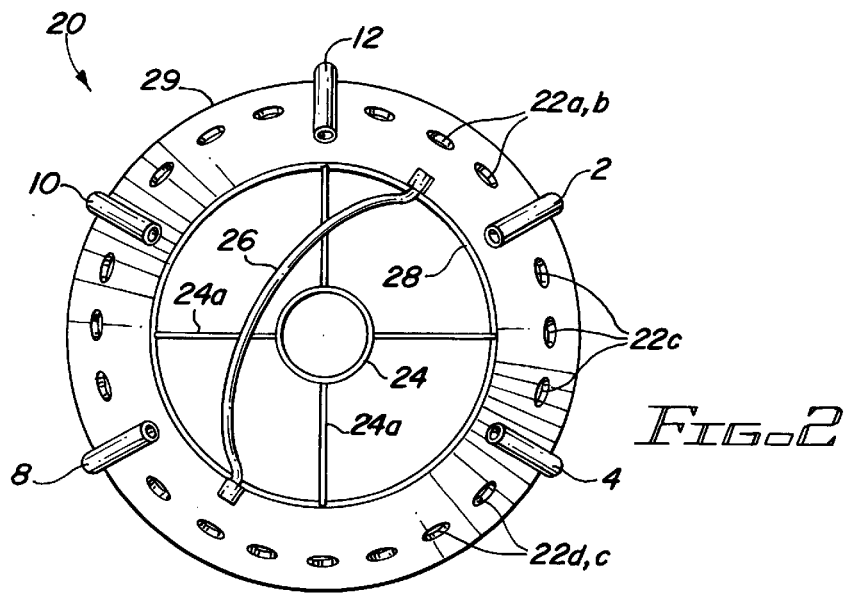
FIG. 2 a top elevational view of the shield body shown in FIG. 1.

Shield body 20 further comprises a plurality of elongated tubular structures 2, 4, 8, 10 and 12 which are operably connected to the shield body for a purpose about to be explained. As best shown in FIG. 9, which illustrates only one of the elongated tubular structures, 4, it is seen that in the preferred embodiment, tubular structures 2, 4, 8, 10, and 12 are disposed along outer shield edge 29, about shield 20, and are set at a predetermined angle relative to the shield body outer edge 29. The predetermined angle of the tubular structures is such that corresponding, imaginary, longitudinal axes 70, (see FIG. 9), extend through each of tubular structures 2, 4, 8, 10 and 12, and will intersect at a common point above shield 20 and breast B, which corresponds a point above the areola A, and ideally, generally above nipple, N. In the preferred embodiment, tubular structures 2, 4, 8, 10 and 12 are also disposed such that their positions are at the 2 o'clock, 4 o'clock, 8 o'clock, 10 o'clock and 12 o'clock positions respectively around shield 20, as best seen in FIGS. 2 and 4. It will be appreciated that the tubular structures must be secure in their orientation about shield body 20, and accordingly, a preferred embodiment of this invention would include angled guides 18 securely fastened to shield body 20, also best seen in FIG. 9 which may comprise a webbing of material formed on the shield body 20 and extending up to each of the elongated tubular structures.

Shield 20 may further comprise means for positioning the shield body 20 on the breast B, in a consistent and accurate manner. The positioning means may comprise an aligning ring, 24 as shown in FIG. 2 which will preferably aid a medical practitioner in positioning shield 20 on breast B. In the preferred embodiment, aligning ring 24 will be sized dimensioned and configured to substantially correspond the outer diameter of nipple N of breast B and areola A, and ideally will include a sight or pair of cross hairs 24a, shown in FIG. 2, for precise positioning of the shield thereover.

Also in the preferred embodiment, shield 20 may be formed to include a lip member 25. As seen in FIGS. 3 and 4, lip member 25 extends from a bottom portion of shield 20, which corresponds the inferior portion of the patient's breast I. Lip member 25 is sized, configured and dimensioned to cover a section of skin corresponding a region under the nipple of the patient's breast, sometimes referred to as the pedicle, which section will be preserved during the surgery in order to maintain the patient's sensation in the breast and also to sustain adequate blood flow in the breast area. It will therefore be understood that lip member 25 covers and therefore protects the pedicle skin section under the breast by preventing the surgeon from cutting into that section.

Figure 1:
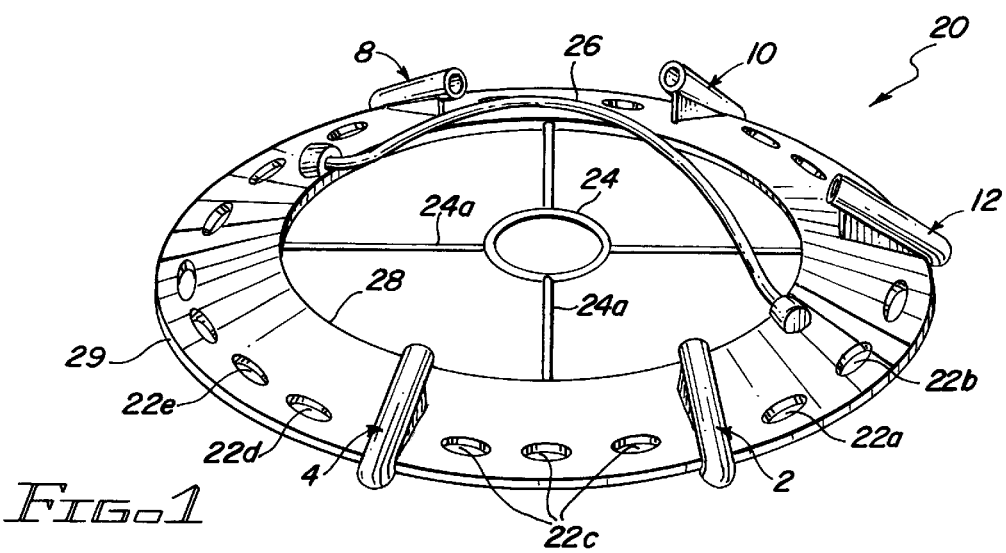
FIG. 1 is an isometric view of the shield body of the present invention.

In the preferred embodiment, shield 20 will also include means for lifting the shield and any breast tissue secured thereto. In particular, the means for lifting may comprise a handle 26 operably connected to an exposed surface of shield body 20. As is about to be described below, handle 26 allows a medical practitioner or surgical assistant using only one hand to readily lift and position breast B for the removal of breast tissue. As seen in FIGS. 1 and 2, handle 26 is preferably secured to shield body 20 at top surface generally near inner body edge 28.

Referring now to FIG. 5, it can be seen that the apparatus of this invention preferably includes a marker 30. Marker 30 comprises an elongate body 34, having a tip 36 at one end, a stopper 32 at or near the other end, and a bovie 38. In the preferred embodiment, body 34, houses an interior chamber in fluid communication with tip 36 which has an opening therein. Also in the preferred embodiment, body 34, of marker 30, is non-conductive along its entire length, except for open tip 36. Marker 30 will preferably be employed by a medical practitioner in conjunction with shield 20 during a breast reduction surgery, as will be described below.

Figure 7A:
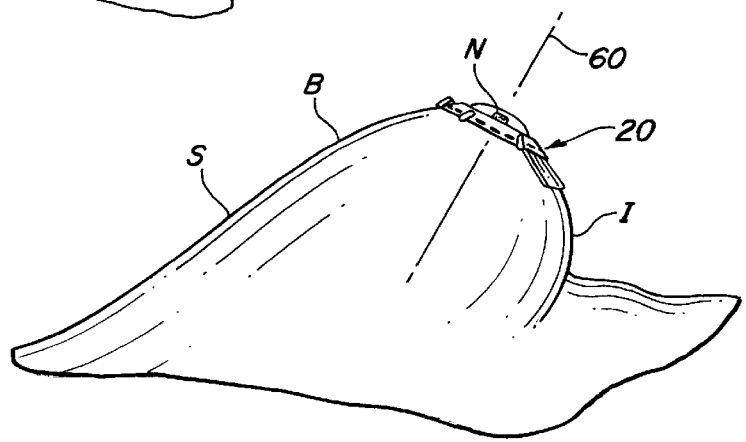
FIG. 7A is a cross-sectional view of the breast seen in FIG. 7 taken along the line A—A.

Referring now to FIG. 6, it can be seen that a typical breast B includes nipple N, areola A, superior portion S and inferior portion I. In FIGS. 7 and 7A, it is shown that shield 20 should be positioned on breast B such that an imaginary axis 60, seen in FIG. 7A, extends longitudinally generally through the center of both nipple N and the center of aligning ring 24. Shield 20 should then be securely, yet removably fastened to breast B, preferably by way of suturing which has been discussed previously. Prior to fastening shield 20 to breast, and in order to achieve the best results, it is desirable to have oriented shield 20 in position on breast B such that the tubular structures are disposed as seen in FIG. 7. That is, with tubular structures 2, 4, 8, 10 and 12 corresponding to the 2, 4, 8, 10 and 12 o'clock positions around breast B respectively.

Figure 8:
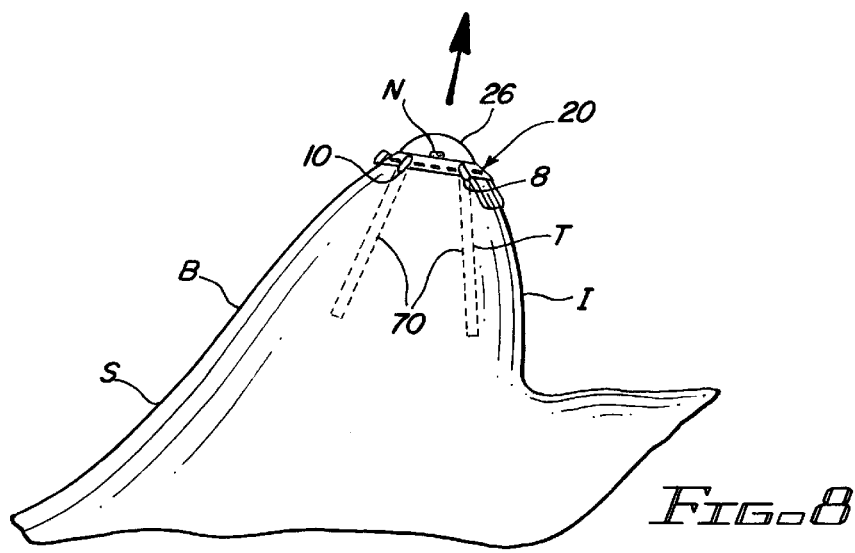
FIG. 8 is a cross-sectional view of the breast seen in FIG. 7A positioned so that a marker may be introduced into the outward projections of the shield body.

In order to ensure that both of the patient's breasts B will be substantially proportionately reduced, a medical practitioner will employ handle 26 to lift breast B until breast B is substantially positioned as seen in FIG. 8. After doing so, the medical practitioner may then insert marker 30 into each of tubular structures 2, 4, 8, 10 and 12.

As an illustrative example, please refer to FIG. 9, and the following description for passing marker 30 through tubular structure 4. Marker 30 should be inserted into top opening 4a, open tip 36 first and should be gently advanced through tubular structure 4 and continued so that tip 36 pierces, penetrates and travels into the breast tissue underneath shield 20, until stopper 32, or another like protrusion on marker 30, contacts and abuts top opening 4a, of tubular structure 4. Band size than top is of a larger diameter and size than top opening 4a of structure 4, the stopper 32 and top opening 4a cooperatively prevent open tip 36 and marker 30 from inadvertently penetrating the patient's chest cavity. In an alternate embodiment, the marker 30 may be formed to have a stopper 32 or other like protrusion which is adjustable along the length of the marker 30 so that the depth of penetration of the marker into a patient's chest can be varied. For example, the stopper 32 may be slidable on and with respect to the marker upon coming into contact with the elongated tubular structure, when the marker 30 is being passed therethrough. In this alternate embodiment, the sliding, adjustable movement of stopper 32 will be within a relatively narrow height range on marker 30 so as to again, prevent inadvertent penetration of the patient's chest cavity by the marker 30 and/or its open tip 36. In the preferred embodiment, marker 30 is non-conductive along its length, except at the tip 36, which should be provided with a source of electrical current. Devices are known in the art for providing electrical current to a tip of an instrument, such as electrolysis instruments and various medical products. Providing the marker 30 with a tip which can be supplied with electric current carries an advantage in that with the help of electricity, the tip can burn through the fatty tissue of the breast. Consequently, marker 30 advances easily, thus avoiding any variation in the angle of entry of marker 30 into the tissue of breast B.

As marker 30 is advanced into breast B, a track T is opened into the tissue of breast B, as seen in phantom FIG. 8. In a preferred embodiment, a medical practitioner may now use marker 30 to mark track T with a dye, such as methylene blue, preferably as marker 30 is withdrawn from track T and tubular structure 4. In the preferred embodiment, marker 30 has a bovie 38 positioned at its upper end. Bovie 38 is well known in the medical community and is adapted to receive a syringe (not shown) for providing dye to the interior chamber of marker body 34. In order to mark track T, a medical practitioner injects a marking dye, from a syringe (not shown), into bovie 38. Bovie 38 communicates the dye through the hollow interior of marker 30 and therethrough open tip 36, thereby marking track T with dye. The entire length of track T may be marked by injected dye into marker 30 as it is withdrawn from track T. Preferably, to facilitate later resecting of the breast B, the entire length of track T should be marked with dye. For purposes of illustration, marker 30 was described as marking track T corresponding to tubular structure 4, although the above marking procedure should be repeated with each of the remaining tubular structures 2, 8, 10 and if desired, 12 also. A medical practitioner may choose to insert marker 30 into tubular structures 2, 4, 8, 10 and 12 in any desired order.

After the tracks T corresponding to tubular structures 2, 4, 8, 10 and 12, have been marked the medical practitioner may divide the mass of the tissue of breast B using tracks T as cutting guides as seen in FIG. 10. In dividing the mass of breast B, a medical practitioner will typically make radial incisions 2', 4', 8' and 10' as seen in FIG. 10. Incisions 2', 4', 8' and 10' correspond to the 2, 4, 8 and 10 o'clock positions around breast B. The medical practitioner will not cut or divide breast B between the 4 o'clock and 8 o'clock positions, thereby preserving the skin on the underside of the breast and forming an inferior base monopolar pedicle. As has been explained, the inferior base monopolar pedicle will ensure that adequate circulation is provided to and sensation maintained within nipple N and areola A. Preferably, a medical practitioner will first cut incisions 2' and 4' and remove breast tissue from between these two incisions, and will next cut incisions 10' and 8' and also remove breast tissue from between these incisions. As seen in FIG. 11, in this procedure a medical practitioner will remove breast tissue from the sides of superior segment S, of breast B, until the desired shape and size of breast B have been achieved. When performed on both of a patient's breasts during the same operation, a medical practitioner may readily shape both breasts so that they are substantially proportionate. This procedure ensures that the patient's left and right breasts will be proportionate and that the nipple and areola have adequate blood circulation and are appropriately positioned on the breasts.

While this invention has been shown and described in what is considered to be a practical and preferred embodiment, it is recognized that departures may be made within the spirit and scope of this invention which should, therefore, not be limited except as set forth in the claims which follow and within the meaning of the doctrine of equivalents.

What is claimed is:

1. A breast reduction apparatus to be used during a surgery to reduce the size of a breast, the breast having a nipple, an areola and superior and inferior portions; said apparatus comprising:

a shield body having an inner edge and an outer edge, and a substantially circular opening extending therethrough, sized, dimensioned and configured to generally correspond the areola of the breast, a plurality of elongated tubular structures, each elongated tubular structure having an elongated body and an opening at a first, top end and an opening at a second, bottom end, and being hollow between said ends, each of said elongated tubular structures secured to said shield body and at a predetermined angle relative to said shield; and means on a shield body for removably fastening said shield body to said breast.

2. A breast reduction apparatus as recited in claim 1, further comprising a means for positioning said shield body on a breast.

3. A breast reduction apparatus as recited in claim 2, wherein said positioning means comprise an aligning ring.

4. A breast reduction apparatus as recited in claim 3, wherein said aligning ring is sized, dimensioned and configured to substantially correspond an outer diameter of a nipple of a breast.

5. A breast reduction apparatus as recited in claim 1, further comprising an angled guide secured to each of said elongated tubular structures and to said outer edge of said shield body, each of said angled guides structured and disposed to give a predetermined angle to each of said tubular structures relative to said shield body.

6. A breast reduction apparatus as recited in claim 5 wherein said elongated tubular structures and said corresponding angled guides are disposed near said outer edge of said shield body in positions generally corresponding the 8 o'clock, 10 o'clock, 12 o'clock, 2 o'clock, and 4 o'clock positions on a clock.

7. A breast reduction apparatus as recited in claim 1 wherein said means for removably fastening said shield body to a breast comprise a plurality of suture openings.

8. A breast reduction apparatus as recited in claim 7 wherein said plurality of suture openings are disposed in a generally circular arrangement on said shield body.

9. A breast reduction apparatus as recited in claim 1 wherein said shield body is slightly dome-shaped in contour.

10. A breast reduction apparatus as recited in claim 1 wherein said shield body further includes a means for lifting said shield body.

11. A breast reduction apparatus as recited in claim 10 wherein said means for lifting said shield body is a handle.

12. A breast reduction apparatus to be used during a surgery to reduce the size of a breast, the breast having a nipple, an areola and superior and inferior portions; said apparatus comprising:

a substantially circular, generally flat yet dome shaped shield body, said shield body having an inner edge and an outer edge, and having a circular opening extending therethrough bounded by said inner edge, said shield body being sized, dimensioned and configured to substantially correspond an areola of a breast and said opening being sized, dimensioned and configured to reveal a large portion of an areola therethrough, means for positioning and centering said shield body on a nipple of a breast about an areola, means for removably fastening said shield body to a breast;

means for lifting said shield body after being fastened to a breast, said shield body including a plurality of angled guides formed on an upper surface thereof and generally along and near said outer edge of said shield body, a plurality of elongated tubular structures, each elongated tubular structure having a top open end, a bottom open end, and being hollow between said ends, each of said elongated tubular segments being secured to a corresponding one of said angled guides, said angled guide disposing said elongated tubular structures at a predetermined angle to said shield body, and a marker having a bovie, an open tip and a stopper, said open tip being structured and disposed to penetrate beneath an epidermal layer of breast tissue, said marker being sized, dimensioned and structured for insertion first into and passage through said elongated tubular structures and then into a breast thereby opening a marking track into a breast secured underneath said shield body, said stopper of said marker being positioned on said marker so that said open tip extends a maximum pre-selected distance below said bottom open end of said tubular structure when said marker is fully inserted into said tubular structure such that said marker is prevented from opening a marking track, into a breast, of greater length than is desired.

13. A breast reduction apparatus as recited in claim 12 wherein said marker includes a chamber between said bovie and said open tip end, said chamber structured for holding fluid and being in fluid communication with said open tip, and said marker further including means structurally connected to said chamber for releasing said fluid out of said chamber and through said open tip end.

14. A breast reduction apparatus as recited in claim 12 wherein said marker includes a hollow interior structured for maintaining fluid therein and for allowing fluid to flow through said hollow interior and to exit at said open tip, and said marker further including means operably connected to said marker for supplying fluid from an outside source to said hollow interior of said marker.

15. A breast reduction apparatus as recited in claim 14 wherein selected portions of said marker are non-conductive.

16. A breast reduction apparatus as recited in claim 12 wherein said stopper is adjustable along the length of said marker.

17. A breast reduction apparatus to be used during a surgery to reduce the size of a breast, the breast having a nipple, an areola and superior and inferior portions; said apparatus comprising:

a generally flat shield body having a substantially circular shape, said shield body including an inner edge and an outer edge, said inner edge defining a substantially circular aperture therethrough, said shield body further including an upper exposed surface and a lower surface, said lower surface being slightly dome-shaped, said shield body further including a lip member extending from a bottom portion of said shield body, said lip member being sized, configured and dimensioned to cover a portion of skin on an underside of the breast, a plurality of elongated tubular structures, each elongated tubular structure having an elongated body and an opening at a first, top end and an opening at a second, bottom end, each of said elongated tubular segments secured to said shield and at a predetermined angle to said shield;

means on said body for removably fastening said shield to said breast, means on said body for positioning said shield on the breast, and means for lifting said shield body and breast tissue connected thereto, after said shield body has been secured to the breast.

18. A breast reduction apparatus to be used during a surgery to reduce the size of a breast, the breast having a nipple, an areola and superior and inferior portions; said apparatus comprising:

a shield body having an inner edge and an outer edge, and a substantially circular opening extending therethrough, a plurality of elongated tubular structures, each elongated tubular structure having an elongated body and an opening at a first, top end and an opening at a second, bottom end, and being hollow between said ends, each of said elongated tubular structures secured to said shield body and at a predetermined angle relative to said shield body, said shield body including an aligning ring disposed within said substantially circular opening, said aligning ring being sized, dimensioned, and configured to substantially correspond an outer diameter of a nipple of a breast, a pair of cross hairs extending from said aligning ring to said shield body for precise positioning of said aligning ring over a nipple; and means on said shield body for removably fastening said shield body to a breast.

19. A breast reduction apparatus to be used during a surgery to reduce the size of a breast, the breast having a nipple, an areola and superior and inferior portions; said apparatus comprising:

a shield body having an inner edge and an outer edge, and a substantially circular opening extending therethrough, a lip member extending from a bottom portion of said shield body, said lip member structured and disposed to cover and generally correspond an inferior portion of a breast;

a plurality of elongated tubular structures, each elongated tubular structure having an elongated body and an opening at a first, top end and an opening at a second, bottom end, and being hollow between said ends, each of said elongated tubular structures secured to said shield body and at a predetermined angle relative to said shield body; and means on said shield body for removably fastening said shield body to a breast.

20. A breast reduction apparatus to be used during a surgery to reduce the size of a breast, the breast having a nipple, an areola and superior and inferior portions; said apparatus comprising:

a substantially circular, generally flat yet dome shaped shield body, said shield body having an inner edge and an outer edge, and having a circular opening extending therethrough bounded by said inner edge, said shield body being sized, dimensioned and configured to generally correspond an areola of a breast and said opening being sized, dimensioned and configured to reveal a large portion of an areola therethrough, means on said shield body for positioning and centering said substantially circular opening of said shield body on a nipple of a breast and about an areola, means on said shield body for removably fastening said shield body to a breast, means on said shield body for lifting said shield body and a breast fastened thereto, said shield body including a plurality of angled guides formed on an upper surface thereof and generally along and near said outer edge of said shield body, a plurality of elongated tubular structures, each elongated tubular structure having a top open end, a bottom open end, and being hollow between said ends, each of said elongated tubular structures being secured to a corresponding one of said angled guides, each one of said angled guides disposing one of said elongated tubular structures at a predetermined angle relative to said shield body, a marker having a bovie, an open tip and a stopper, said open tip being conductive and said marker being sized, dimensioned and structured for insertion into and passage through said elongated tubular structures and then into a breast thereby opening a marking track into a breast, said stopper of said marker being positioned on said marker so that said open tip extends a maximum pre-selected distance below said bottom open end of one of said elongated tubular structures when said marker is fully inserted into said tubular structure, such that said marker is prevented from opening a marking track, into a breast, of a greater length than is desired; and said marker including a hollow interior structured for maintaining fluid therein and for allowing fluid to flow and exit said open tip, and said marker further including means operably connected to said marker for supplying fluid from an outside source to said hollow interior of said marker.

21. A breast reduction apparatus to be used during a surgery to reduce the size of a breast, the breast having a nipple, an areola, and superior and inferior portions; said apparatus comprising:

a shield body having an inner edge and an outer edge, and a substantially circular opening extending therethrough sized, dimensioned and configured to generally correspond an areola of a breast, a plurality of elongated tubular structures, each elongated tubular structure having an elongated body with an opening at a first, top end and an opening at a second, bottom end, and being hollow between said ends, each of said elongated tubular structures fixed on said shield body generally near said outer edge and at a predetermined angle relative to said shield body; and means on said shield body for removably fastening said shield body to a breast.

\* \* \* \* \*